(12) United States Patent
Stump et al.

(10) Patent No.: US 9,059,548 B2
(45) Date of Patent: Jun. 16, 2015

(54) ADAPTER FOR MECHANICALLY AND ELECTRICALLY CONNECTING AN IMPLANTABLE ELECTRODE TO AT LEAST ONE TEST TERMINAL CONTACT

(71) Applicant: BIOTRONIK SE & Co. KG, Berlin (DE)

(72) Inventors: Joachim Stump, Berlin (DE); Klaus Bartels, Berlin (DE); Marion Mieke, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 106 days.

(21) Appl. No.: 13/911,709

(22) Filed: Jun. 6, 2013

(65) Prior Publication Data

US 2013/0337674 A1    Dec. 19, 2013

Related U.S. Application Data

(60) Provisional application No. 61/660,838, filed on Jun. 18, 2012.

(51) Int. Cl.
| | |
|---|---|
| H01R 13/62 | (2006.01) |
| H01R 24/04 | (2006.01) |
| H01R 24/28 | (2011.01) |
| A61N 1/375 | (2006.01) |
| A61N 1/372 | (2006.01) |

(52) U.S. Cl.
CPC .............. *H01R 24/28* (2013.01); *H01R 13/62* (2013.01); *A61N 1/375* (2013.01); *A61N 1/372* (2013.01)

(58) Field of Classification Search
CPC ........ H01R 24/28; H01R 13/62; H01R 24/58; H01R 2107/00; H01R 2201/12; H01R 13/703; H01R 13/5224; A61N 1/3752; A61N 1/375; A61N 1/3754

USPC ............ 439/638, 909, 300, 668–669; 607/37
See application file for complete search history.

(56) References Cited

U.S. PATENT DOCUMENTS

| | | |
|---|---|---|
| 5,354,326 A | 10/1994 | Comben et al. |
| 7,777,140 B2 | 8/2010 | Cappa et al. |
| 8,147,275 B1 * | 4/2012 | Drake et al. .................. 439/638 |
| 8,480,427 B2 * | 7/2013 | Marshalok .................... 439/504 |

(Continued)

OTHER PUBLICATIONS

European Search Report and Notes to the European Search Report on European Patent Application No. EP 13 16 8212, dated Sep. 3, 2013 (7 pages).

*Primary Examiner* — Xuong Chung Trans
(74) *Attorney, Agent, or Firm* — Buchanan Ingersoll & Rooney PC

(57) ABSTRACT

An adapter for mechanically/electrically connecting an implantable electrode, via the proximal connector thereof including at least one connecting contact for the electrode, to at least one test terminal contact of a measuring device, includes an electrically insulating adapter housing, a connector receiving element adapted to connector shape, and at least one contact element disposed in the adapter housing establishing contact between the at least one connecting contact of the connector and the at least one test terminal. A receiving tray, having the receiving element for the connector, is mounted on the adapter housing and variable between open and closed contact positions. In the open position, the connector is inserted in the receiving element in a defined position and removed therefrom. In the contact position, the at least one connecting contact of the connector is brought in contact with the contact element in the adapter housing in a defined manner.

17 Claims, 15 Drawing Sheets

(56) References Cited

U.S. PATENT DOCUMENTS

| | | |
|---|---|---|
| 8,692,556 B2 * | 4/2014 | Makihara .................. 324/426 |
| 2002/0095079 A1 | 7/2002 | Putz |
| 2005/0177199 A1 | 8/2005 | Hansen et al. |
| 2006/0030918 A1 | 2/2006 | Chinn et al. |
| 2006/0258193 A1 | 11/2006 | Hoecke et al. |
| 2008/0015668 A1 | 1/2008 | Soukup |
| 2012/0130397 A1 | 5/2012 | Reddy et al. |

* cited by examiner

ADAPTER FOR MECHANICALLY AND ELECTRICALLY CONNECTING AN IMPLANTABLE ELECTRODE TO AT LEAST ONE TEST TERMINAL CONTACT

CROSS-REFERENCE TO RELATED APPLICATIONS

This patent application claims the benefit of U.S. Provisional Patent Application No. 61/660,838, filed on Jun. 18, 2012, which is hereby incorporated by reference in its entirety.

TECHNICAL FIELD

The present invention relates to an adapter for mechanically and electrically connecting an implantable electrode, by means of the proximal connector thereof comprising at least one connecting contact for an electrode surface of the electrode, to at least one test terminal contact, in particular to an alligator clip, of a measuring device.

BACKGROUND

With respect to the background of the present invention, reference is made that, for example, cardiac pacemakers, or so-called ICDs (intracardiac devices), comprise implantable stimulation electrodes for electrically connecting the stimulation device to a desired body tissue location. Implantable stimulation electrodes, for example, generally comprise measuring/pacing electrodes, shock electrodes, epicardial electrodes, endocardial electrodes, atrial or ventricular electrodes, unipolar or bipolar electrodes, and the like.

Such stimulation electrodes comprise one or more electrode surfaces at the distal end of the electrode and a connector at the proximal end of the electrode. The latter is used as an interface to the implantable stimulation unit.

When an implantable electrode is implanted in the patient, it is generally recommended to carry out several preliminary tests before permanently fixing the electrode in the final place thereof and before connecting the connector of the electrode to the implanted stimulation unit. For this purpose, the connector of the electrode is temporarily connected to a measuring device, for example, a patient system analysis unit, whereby a series of stimulation pulses of varying energy levels or other test signals can be supplied to the temporarily inserted electrode.

This measuring device is connected to the connector of the electrode by way of test terminal contacts, for example, in the form of alligator clips.

A problem with connecting such test terminal contacts to the connector of the electrode will be briefly highlighted hereafter based on the example of alligator clips.

The direct clip-connection of the alligator clip to the connector is not very reliable in general terms because the alligator clips may detach from the connector during the test operation. Moreover, a poor contact connection may exist if the alligator clips are poorly positioned at the connecting contacts of the connector, and this poor connection can influence the tests and result in incorrect conclusions, for example, with respect to the positioning of the electrode. In addition, faulty contacting and short circuits may occur with careless use of such alligator clips.

In connection with this problem, the prior art provides some solutions. For example, U.S. Pat. No. 7,777,140 discloses a type of contact clip, the clip jaws of which in each case accommodate the individual contact elements for the connecting contacts of the electrode connector. However, since the connector is inserted between the clip jaws, the connecting contacts of the electrode connector are not fully protected from contact. In addition, the connector may be incorrectly inserted in the contact clip, whereby the overall connecting safety of this known adapter solution is not adequate.

Other adaptation solutions are shown in U.S. Pat. No. 5,354,326 and U.S. Pat. No. 7,753,696. All of these solutions have a common drawback that a precisely fit orientation of the test terminal contacts with the connecting contacts of the connector of the electrode is difficult. Especially with the adapter solutions shown in the aforementioned documents, often times a mandrin replacement, required by users of such electrodes, is not possible when the connector is in the inserted position in the adapter during the implantation procedure.

The present invention is directed toward overcoming one or more of the above-identified problems.

Starting from at least the problems of the prior art described above, it is an object of the present invention to create an adapter for mechanically and electrically connecting an implantable electrode to a measuring device, wherein the adapter allows simple and safe adapter handling and, more particularly, improved positioning of the connecting contacts of the electrode and the test terminal contacts of the measuring device with respect to each other.

SUMMARY

At least this object is achieved by an adapter having the following features according to at least one of the independent claim(s):
  an adapter housing made of an electrically insulating material;
  a receiving element for the connector which is adapted to the shape of the connector;
  at least one contact element disposed in the adapter housing for establishing contact between the at least one connecting contact of the connector and the at least one test terminal;
  a receiving tray, which is mounted on the adapter housing so as to be variable between an open position and a closed contact position, and in which the receiving element for the connector is disposed, wherein
    in the open position, the connector can be inserted in the receiving element in a defined position and be removed therefrom; and
    by transferring the receiving tray into the contact position, the at least one connecting contact of the connector can be brought in contact with the contact element in the adapter housing in a defined manner.

By inserting the connector in a receiving tray that is mounted in a defined manner in the adapter housing so as to be variable between the open and contact positions, the receiving tray serves as a positioning aid for the connector, which thus meets the requirement of being correctly brought in connection with the test terminal contacts in the contact position of the receiving tray. The receiving tray thus receives the connector in a correct position and feeds the connecting contacts thereof in a defined and precise manner to the contact elements disposed in the adapter housing, whereby safe electrical contact to the measuring device is established, for example, by way of alligator clips. Because the latter are not placed directly on the connecting contacts of the connector of the electrode, the electrode connector is effectively protected from damage, such as, for example, scratches or deformations.

A variety of mounting designs are conceivable for the receiving tray on the adapter housing, however, two advantageous embodiments are preferred. For one, the receiving tray may be a drawer that can be displaced between the open and closed contact positions on the adapter housing, the displacement direction of the drawer then preferably extending transversely to the longitudinal direction of the connector.

Secondly, the receiving tray may also be designed as a folding tray that can be pivoted between the two aforementioned positions, wherein the pivoting direction can then be again transversely to the longitudinal direction of the connector.

The two aforementioned refinements are relatively easy to implement in terms of design.

In a further preferred embodiment, the receiving tray can be fixed in the open and/or closed contact positions relative to the adapter housing by way of a latching engagement. Both positions preferably have latching engagements. Because of the detent function in the open position, controlled positioning and insertion of the connector in the adapter are possible. The latching engagement of the closed receiving tray in the contact position (i.e., the close position) prevents inadvertent opening and prevents the electrode from falling out of the adapter.

The operating comfort and handling safety of the adapter according to the present invention can be further increased by designing the latching engagement to be detachable by way of a trigger button. The latter can be coupled to the adapter housing, for example, via a spring tongue that is integrally connected to both. The trigger button design can thus be easily implemented using mold features of the adapter housing that are easy to produce from an injection molding point of view.

According to a further preferred embodiment, the connecting contacts of the connector can be completely covered toward the outside in the contact position of the receiving tray. This offers effective protection from contact when handling the electrode in conjunction with the adapter according to the present invention.

Moreover, in front of the connector positioned in the receiving tray, the receiving tray and the adapter housing may be provided at their end faces with an opening to provide unobstructed access to a central electrode lumen guided through the connector, both in the open position and in the contact position. This refinement of the present invention allows simple replacement of a mandrin that is inserted in the central lumen of the electrode, without having to separate the adapter and connector. This advantage is absent in the types of contacting of the adapters shown in the aforementioned prior art.

Further preferred embodiments relate to the contact element in the adapter housing, which may comprise an outwardly exposed contact surface for each test terminal contact. Preferably, a corresponding guide for the test terminal contact flanks each contact surface. For example, alligator clips can thus be safely placed on the adapter and be brought into electrical connection with the contact element thereof.

In general, connectors of implantable electrodes comprise several connecting contacts. The adapter according to the present invention for such a connector may thus comprise two contact elements, which in each case are to be brought into connection with a connecting contact of the connector in the receiving tray and with a test terminal contact of a measuring device.

To assure safe handling of the adapter and of the measuring device to be connected thereto, a polarity symbol may be associated with each of the exposed contact surfaces of the contact elements for the test terminal contacts.

According to a further preferred embodiment, the adapter housing comprises two or four contact elements, for example, for use with pacing or defibrillator electrodes. Eight and more contact elements are also conceivable for other applications, as will be appreciated by one skilled in the art.

Further features, aspects, objects, advantages, and possible applications of the present invention will become apparent from a study of the exemplary embodiments and examples described below, in combination with the figures, and the appended claims.

DESCRIPTION OF THE DRAWINGS

Further characteristics, details and advantages of the invention will be apparent hereafter from the description of exemplary embodiments based on the accompanying drawings. In the drawings.

DETAILED DESCRIPTION

Figure 3:
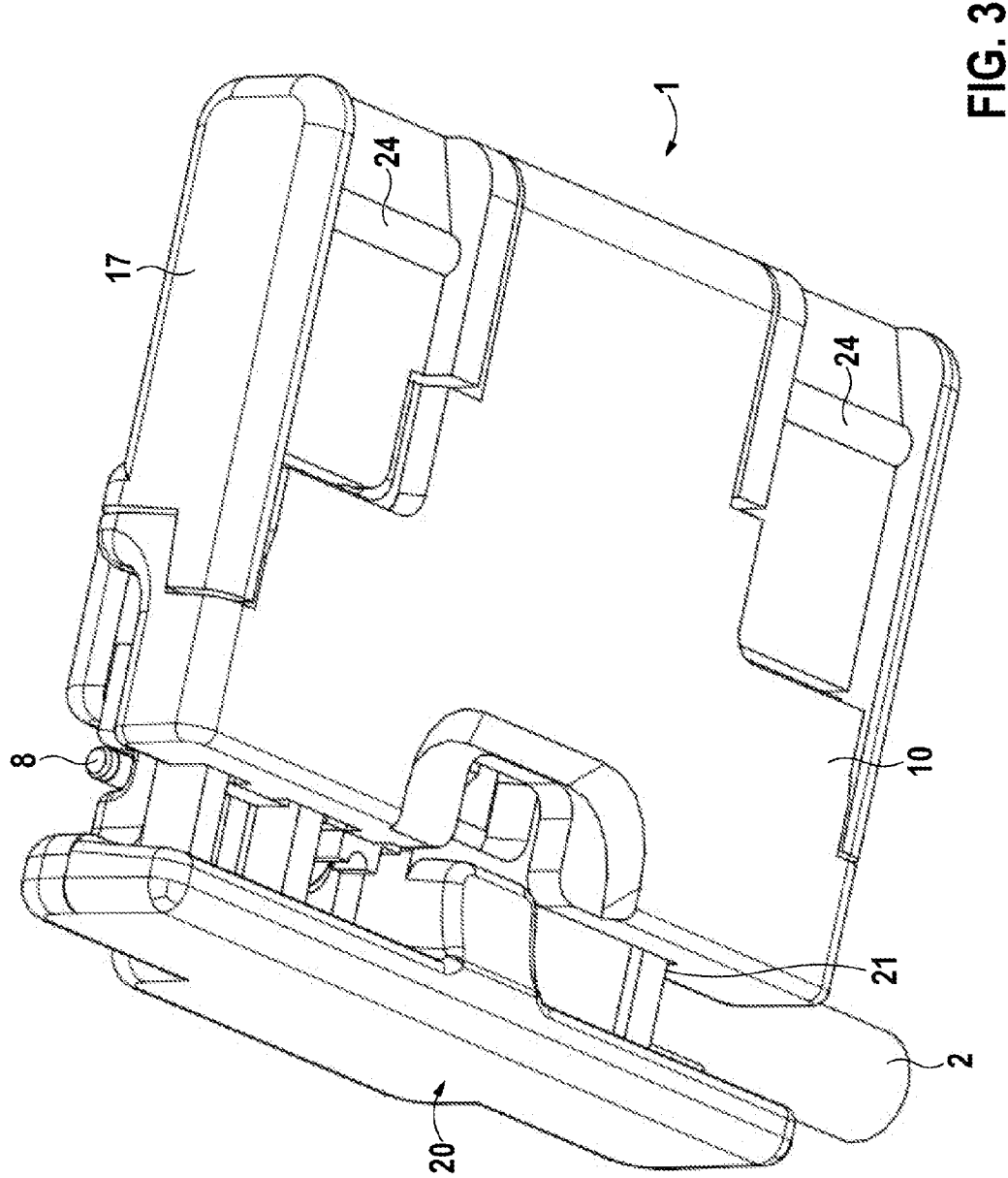
FIGS. 3-4 show perspective views analogous to FIGS. 1-2, obliquely from below.
Figure 4:
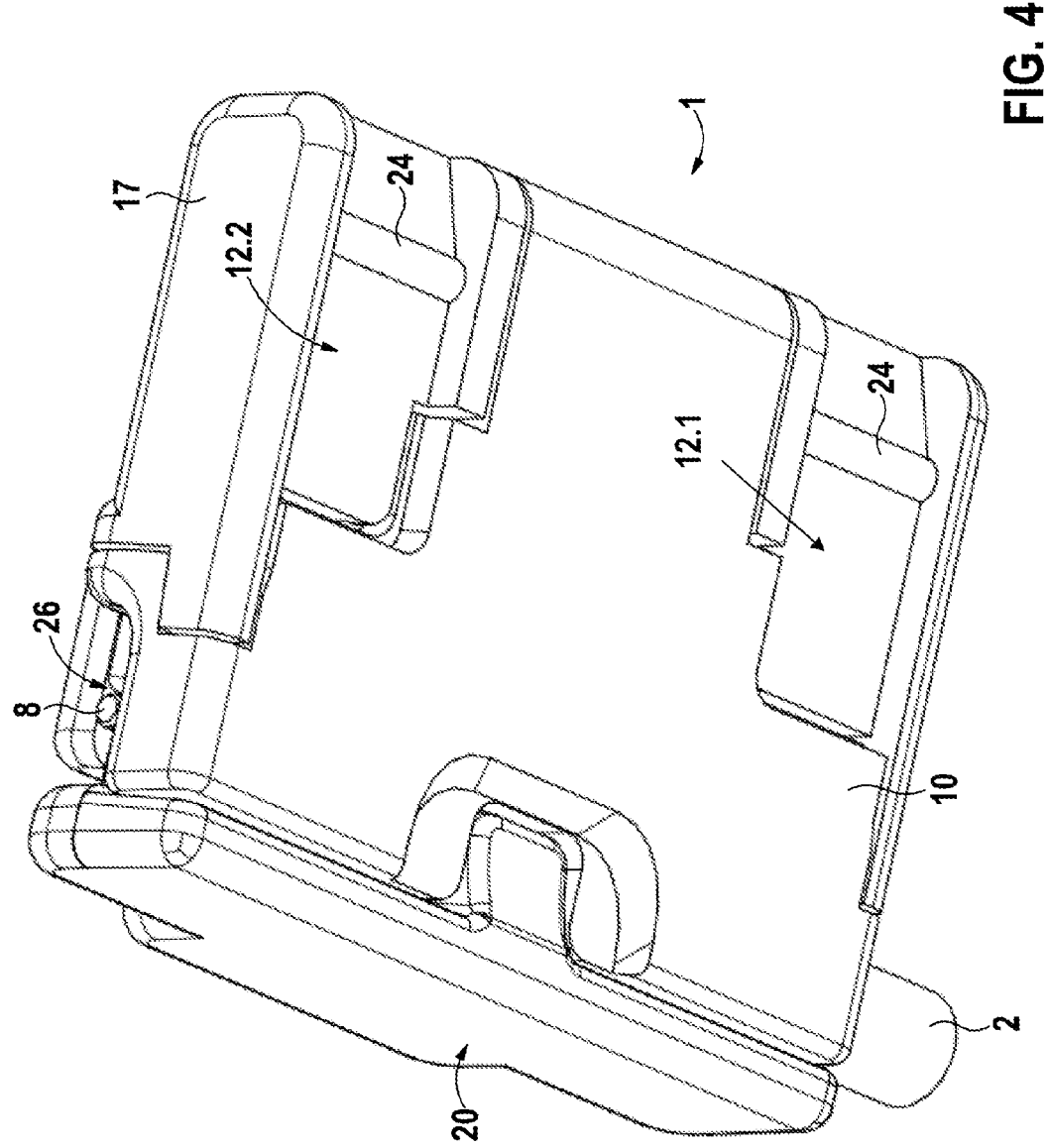
Figure 5:
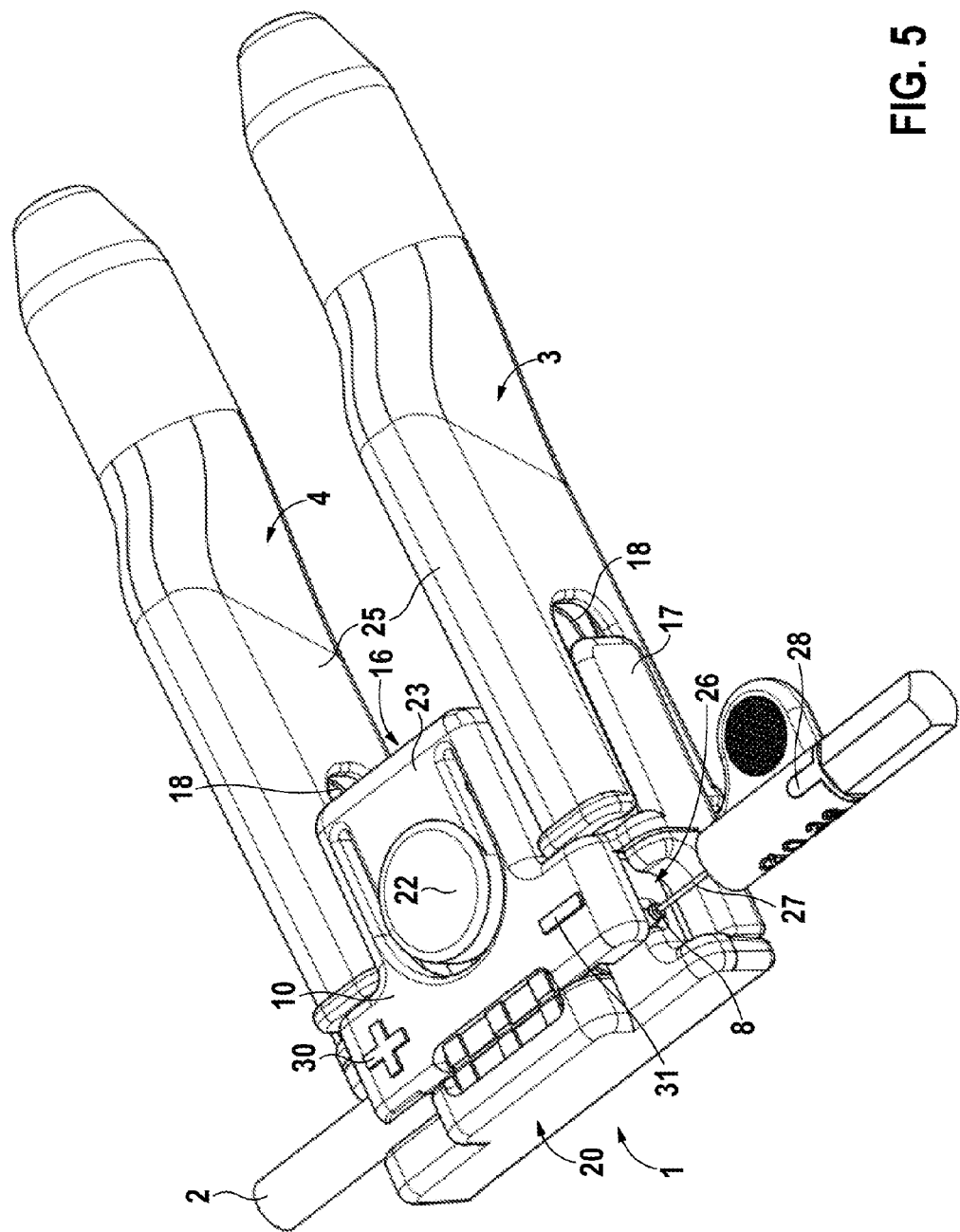
FIG. 5 is a perspective view of the adapter according to FIG. 2 comprising connected alligator clips and an inserted mandrin.
Figure 6:
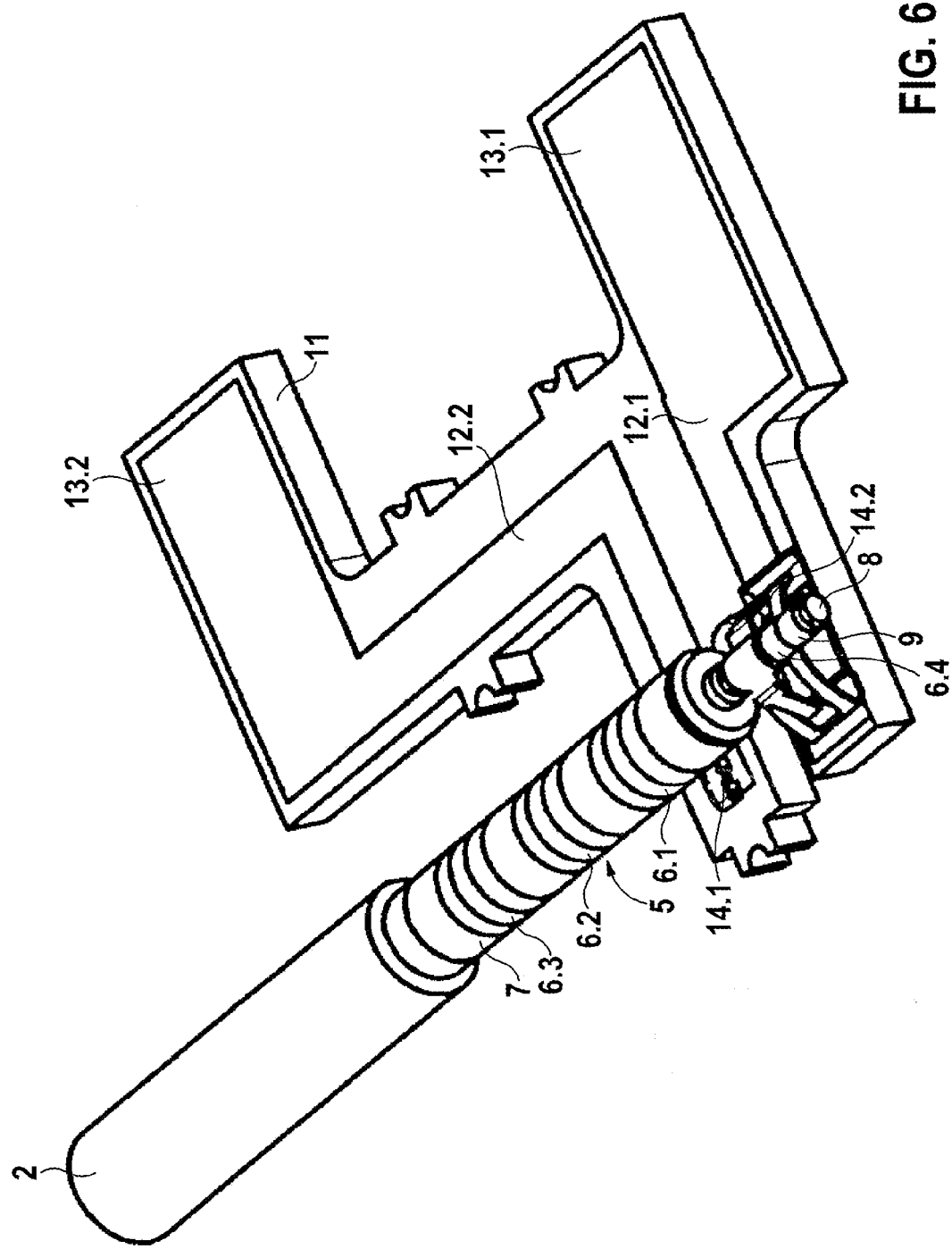
FIGS. 6-7 show a perspective detailed view of a circuit board to be inserted in the adapter and a cut-away perspective view of the adapter, respectively.
Figure 7:
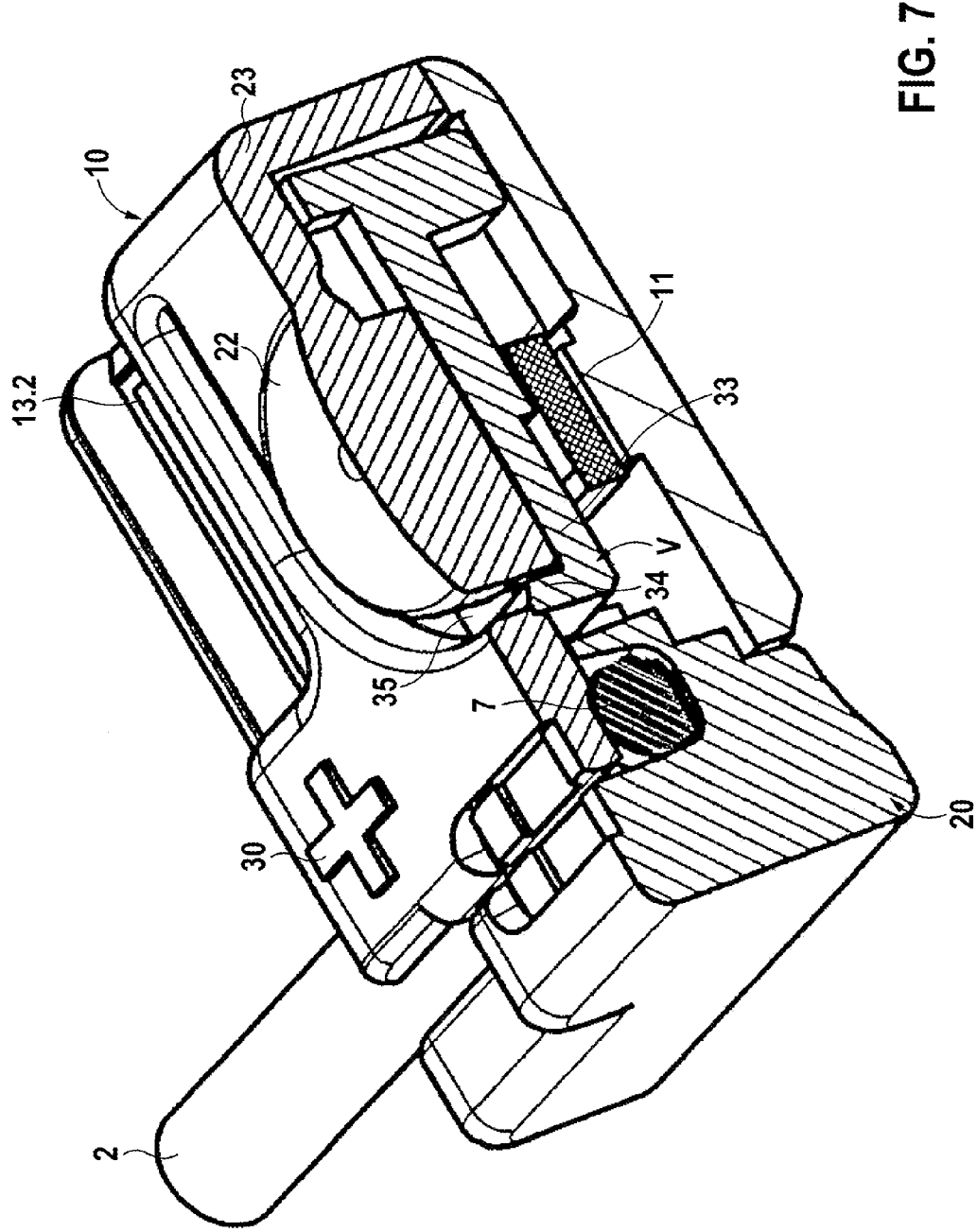
Figure 8:
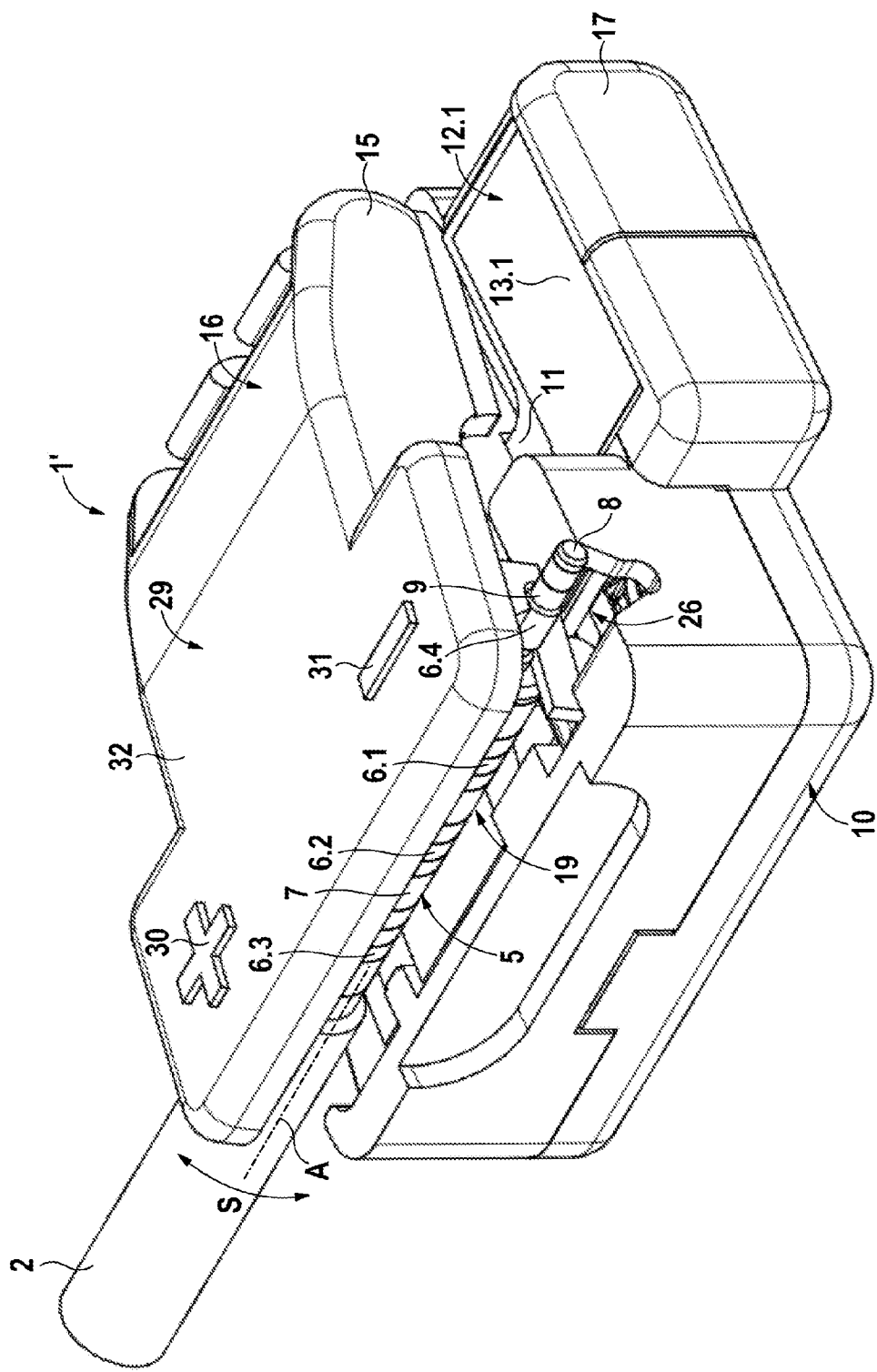
FIGS. 8-9 show perspective views, obliquely from above, of an adapter in a second embodiment comprising a connector in the open and contact positions of the adapter folding tray.
Figure 9:
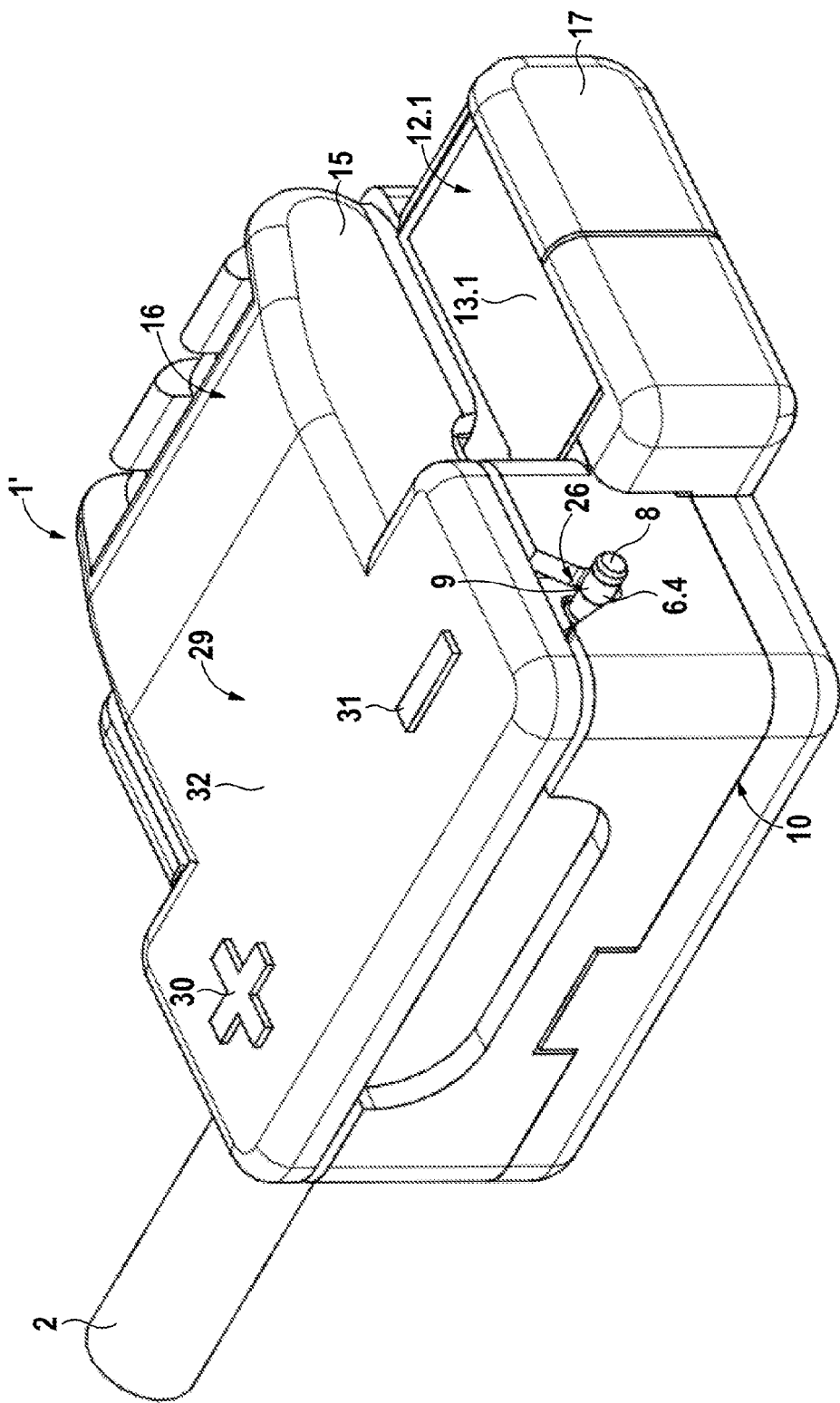
Figure 10:
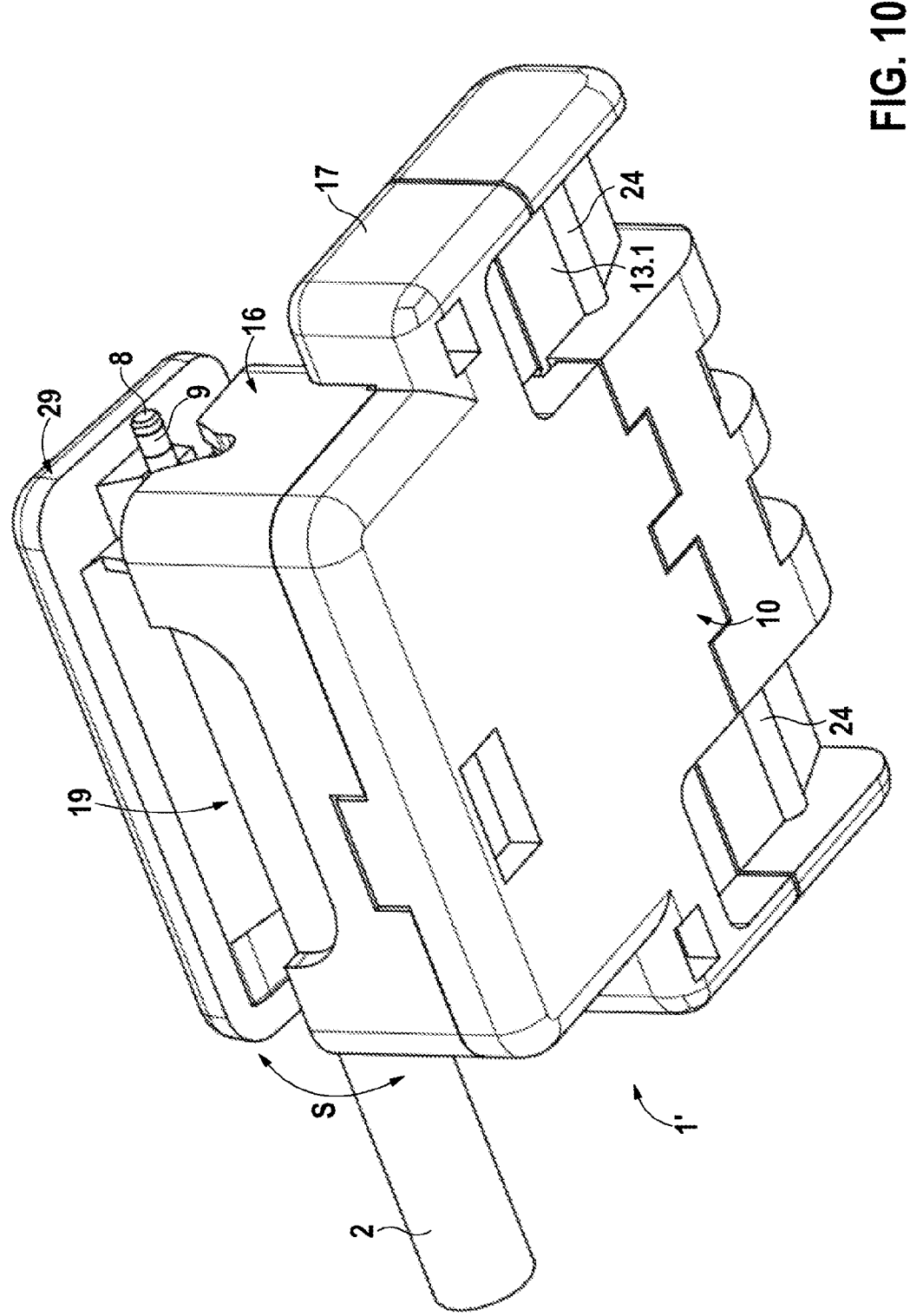
FIGS. 10-11 are perspective views, obliquely from beneath, analogous to FIGS. 8-9.
Figure 11:
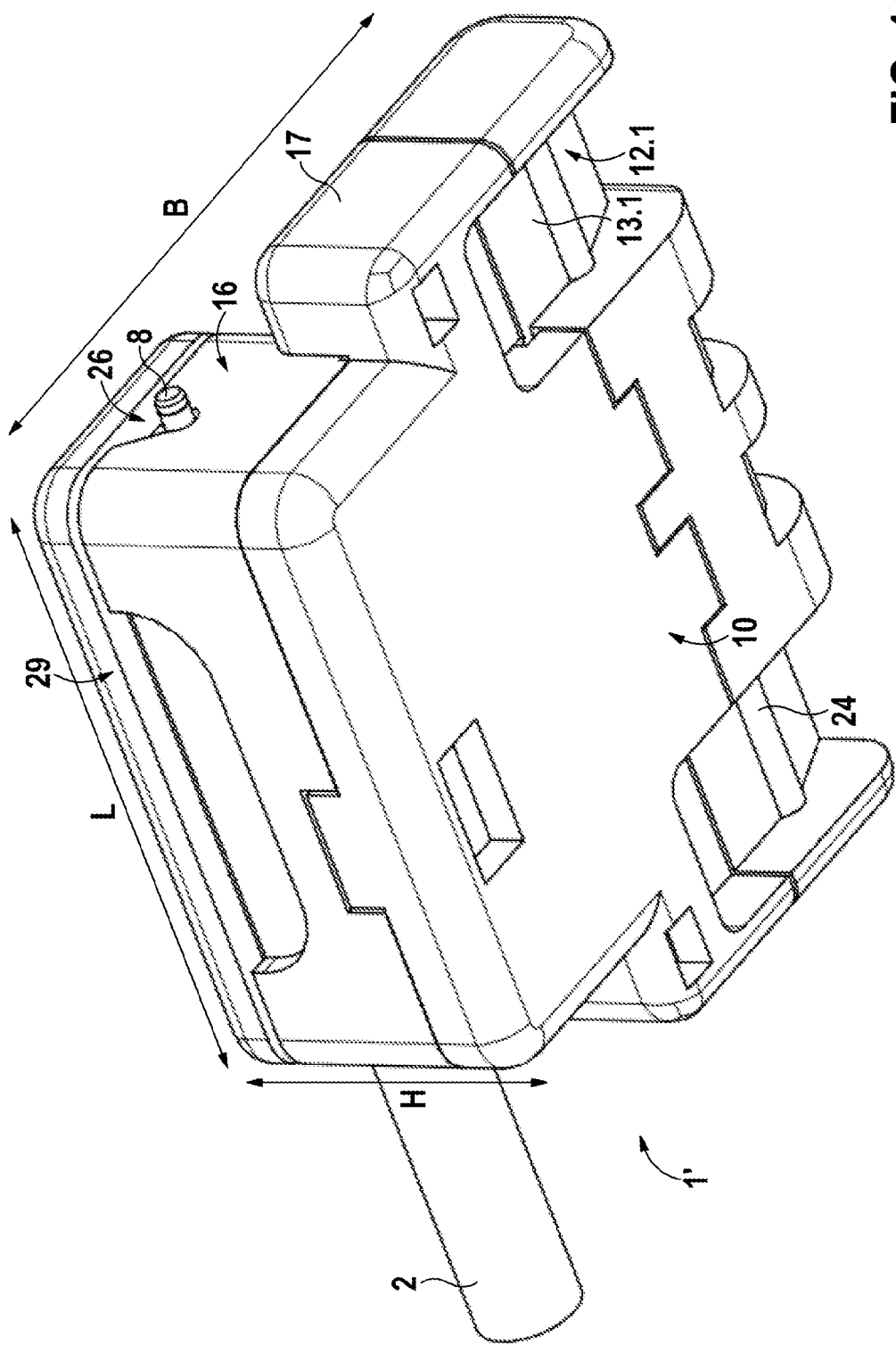

FIGS. 1-7 show a first embodiment of an adapter 1 for mechanically and electrically connecting an implantable electrode 2, which is shown in a cut-away view in the drawings, to a measuring device, which is not shown in detail, with the aid of test terminal contacts, as shown by way of example in FIGS. 5 and 10 in the form of alligator clips 3, 4. At the proximal end, which is apparent especially from FIGS. 1, 8 and 13, the electrode 2 comprises a connector 5, which has four connecting contacts, three 6.1, 6.2, 6.3 in the form of annular surfaces on the connector body 7, and a contact 6.4 on a pin 9 at the connector tip. The electrode 2 further comprises a central lumen 8, which is guided out at the end of the electrode 2 via the pin 9 extending coaxially to the electrode 2.

The adapter housing 10 has a segmented outer shape, the rough contour of which can be described as being cuboid having a length L, width B and height H. It is made of an electrically insulating material, such as an injection molded plastic material, for example.

A circuit board 11 comprising two contact elements 12.1, 12.2 in the form of metallic contact strips is inserted in the adapter housing 10, wherein FIGS. 1-4 and 6 show the exposed contact surfaces 13.1, 13.2 used to connect the alligator clips 3, 4. In the connecting region to the connector 5, spring contacts 14.1, 14.2, which in each case are fixed to the circuit board 11, are electrically connected to the contact elements 12.1, 12.2 and establish the contact with the connecting contacts 6.3 and 6.4 of the electrode 2 when the adapter 1 is closed (see FIG. 6). The guides formed by the side walls 15 of the structure 16 on the adapter housing 10 and the protruding narrow sides 17 receive the "mouth" 18 of the alligator clips 3, 4 (see FIGS. 5 and 12), wherein clamping safety is further increased by the ridges 24 at the lower face of the adapter housing 10.

Figure 1:
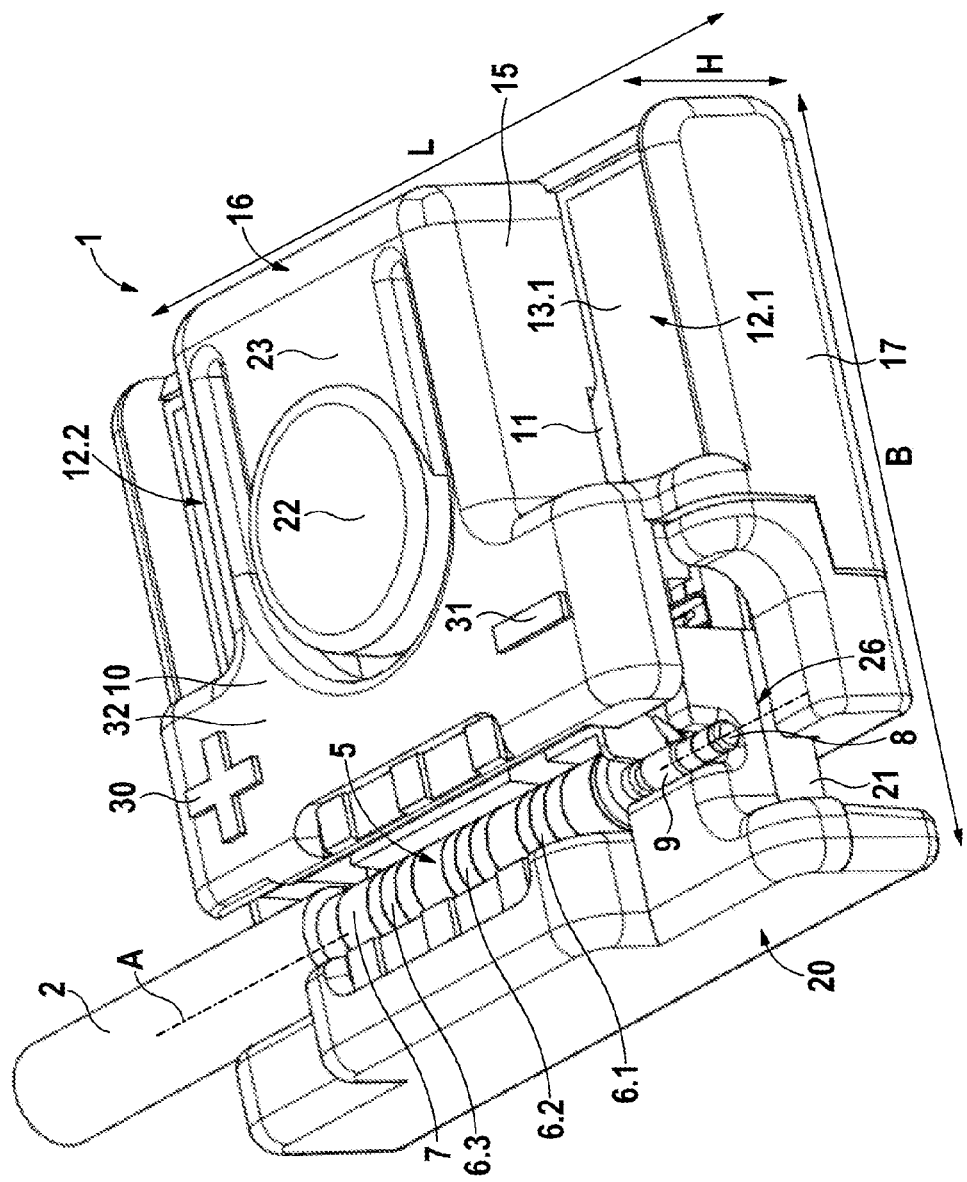
FIGS. 1-2 show perspective views, obliquely from above, of an adapter comprising a connector in the open and contact positions of the adapter drawer with the trigger button.

A receiving element 19, which in the exemplary embodiment shown in FIGS. 1-7 is disposed in a drawer 20, is provided for the connector 5 in the adapter 1. This receiving element 19 corresponds to the shape of the connector 5, whereby the connector 5 is received in the correct position and in a precisely defined manner in the drawer 20, as is shown in FIG. 1.

Figure 2:
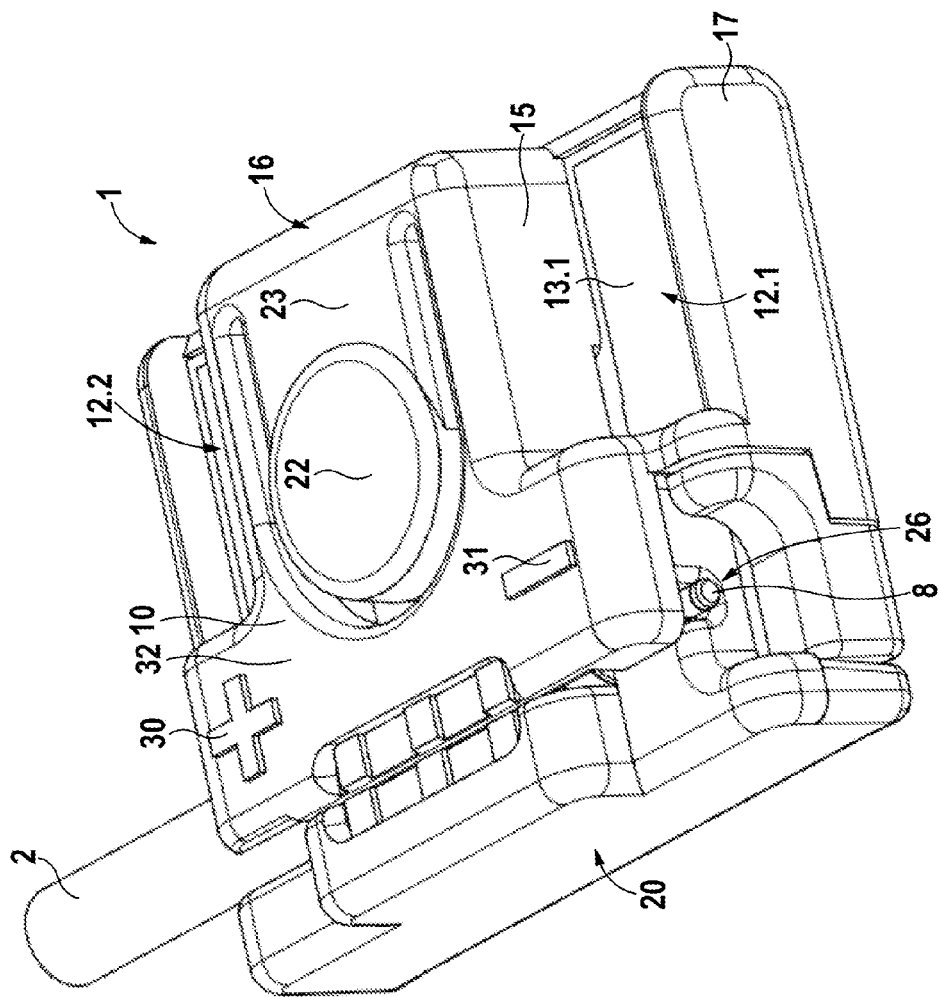

The position of the drawer 20 can be varied in the direction of the width B of the adapter housing 10 between the open position shown in FIGS. 1 and 3 and the contact position shown in FIGS. 2, 4 and 5 and, more specifically, it is mounted on the adapter housing 10 dispaceably by way of corresponding guides 21. In the open position according to FIGS. 1 and 3, in which the connector 5 is inserted in the receiving element 19, and in the contact position shown in FIGS. 2 and 4, the drawer 20 is latched relative to the adapter housing 10. The latching engagement V is formed by a detent tongue 33, which is configured on the drawer 20 and which, with a projection 34, engages in a detent recess 35 in the adapter housing 10 in front of a trigger button 22, which is apparent in FIGS. 1, 2, 5 and 7 and by means of which an elastic spring tongue 23 is connected to the adapter housing 10 so as to be displaceable in the direction of the height H. The latching engagement V can be removed by the trigger button 22 by pressing the same, whereby the projection 34 is lifted out of the detent recess 35. The drawer 20 is thus freely movable.

From the open position shown in FIGS. 1 and 3, the drawer 20 is pushed with the inserted connector 5 transversely to the longitudinal direction A of the connector into the adapter housing 10. In the contact position of the drawer 20, shown in FIGS. 2, 4 and 5, the two connecting contacts 6.3 and 6.4 are electrically guided out via the spring contacts 14.1, 14.2 of the contact elements 12.1, 12.2. By the latching engagement of the drawer 20 in this contact position, a safe connection is provided between the connector 5 and the contact elements 12.1, 12.2.

As shown in FIG. 5, a respective alligator clip 3, 4 is pushed thereon. The seat of the clip on the contact elements 12.1, 12.2 is further improved by ridge-shaped configurations 24 on the lower face of the adapter housing 10, as shown in FIGS. 3 and 4. These ridges are intended to prevent the alligator clips 3, 4 from sliding off. Since the alligator clips 3, 4 are covered toward the outside, together with the contacts thereof, by insulating shoes 25, in the overall a clean contact connection, which is protected from contact, is implemented between a measuring device and the connector 5 via the alligator clips 3, 4 and the adapter 1.

As is further shown in FIG. 5, the drawer 20 and the adapter housing 10 comprises an opening 26, by way of which the pin 9 with the lumen 8 of the electrode 2 can also be accessed in an unobstructed manner in the contact position, shown in FIGS. 2, 4 and 5. The mandrin 27, which is shown in FIG. 5, can thus be easily replaced by pulling it by the handle 28 thereof, or it can be actuated in another manner, without requiring any change to the positioning of the connector and adapter 1.

FIGS. 8-12 show a second embodiment of the adapter 1'. This differs from the embodiment according to FIGS. 1-7 in the design of the receiving tray. This tray is implemented by a folding tray 29, which is mounted on the adapter housing 10 pivotably about a pivot axis S extending parallel to the length. In the open position shown in FIGS. 8 and 10, the folding tray 29 is folded up, whereby the receiving element 19 is accessible laterally for the connector 5 of the electrode 2 (see FIGS. 8 and 10).

The connector 5 inserted in the receiving element 19 is pushed into the adapter housing 10 by the pivoting motion about the pivot axis S and is internally connected there mechanically and electrically to the contact elements 12.1, 12.2. The latter are designed analogous to the exemplary embodiment of FIGS. 1 to 7 and, thus, do not require explanation again. All of the components of the adapter 1' which correspond with those of the adapter 1 according to FIGS. 1-7 are denoted by identical reference numerals, whereby reference can be made to the description according to FIGS. 1-7. It shall be added that the folding tray 29 can likewise be latched in the open and contact positions according to FIGS. 8 and 10, and also FIGS. 9, 11 and 12. The latching engagement is achieved by simple pressing or pulling on the folding tray 29. A trigger button is not provided here.

Figure 12:
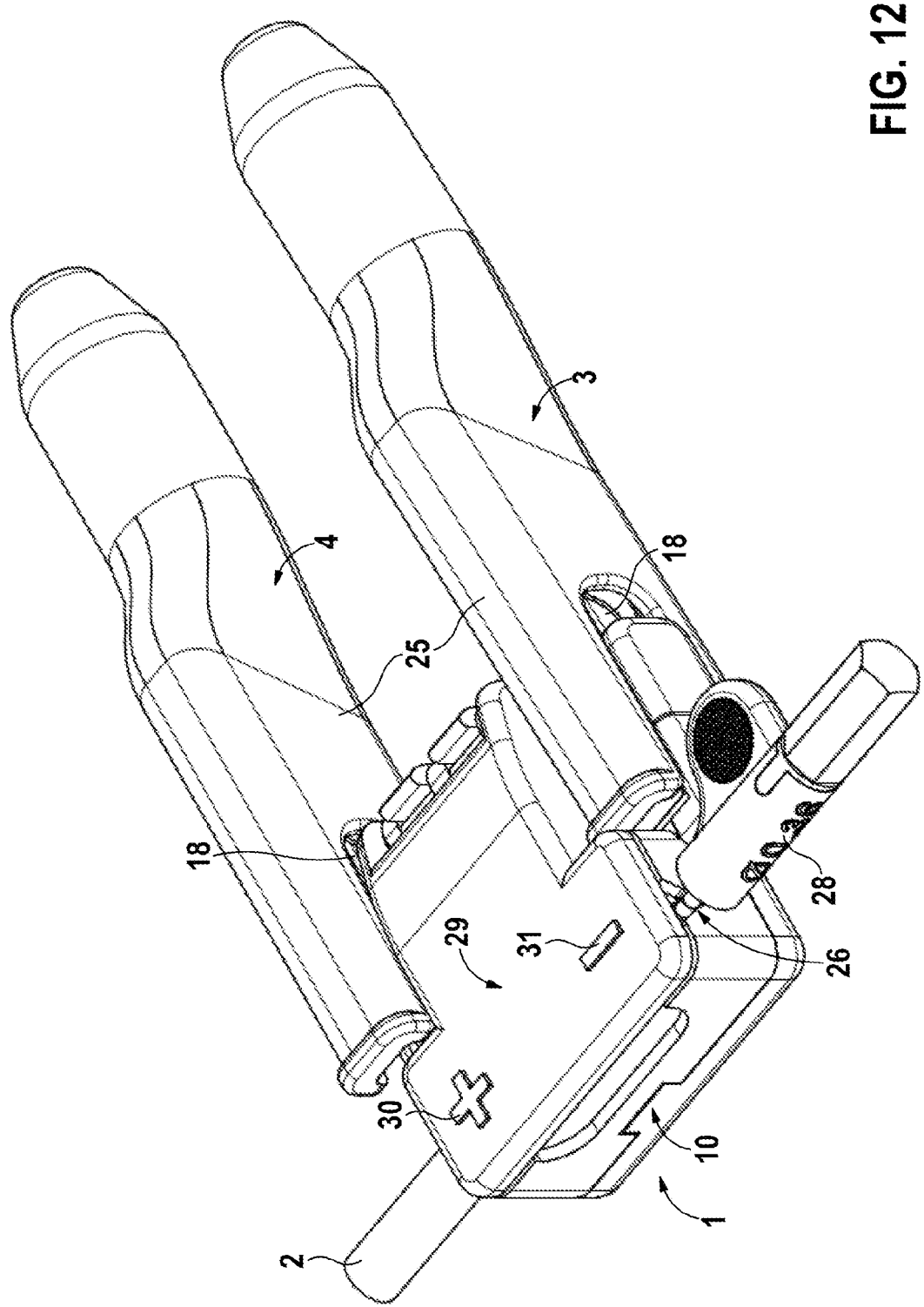
FIG. 12 is a perspective view of the adapter according to FIG. 9 comprising connected alligator clips and an inserted mandrin.

It is important to mention that—as shown in FIG. 12—the adapter 1' is also designed to allow, via an opening 26, a mandrin 27 to be suitably maneuvered via the handle 28 thereof during the connection of a measuring device by the alligator clips 3, 4.

Figure 13:
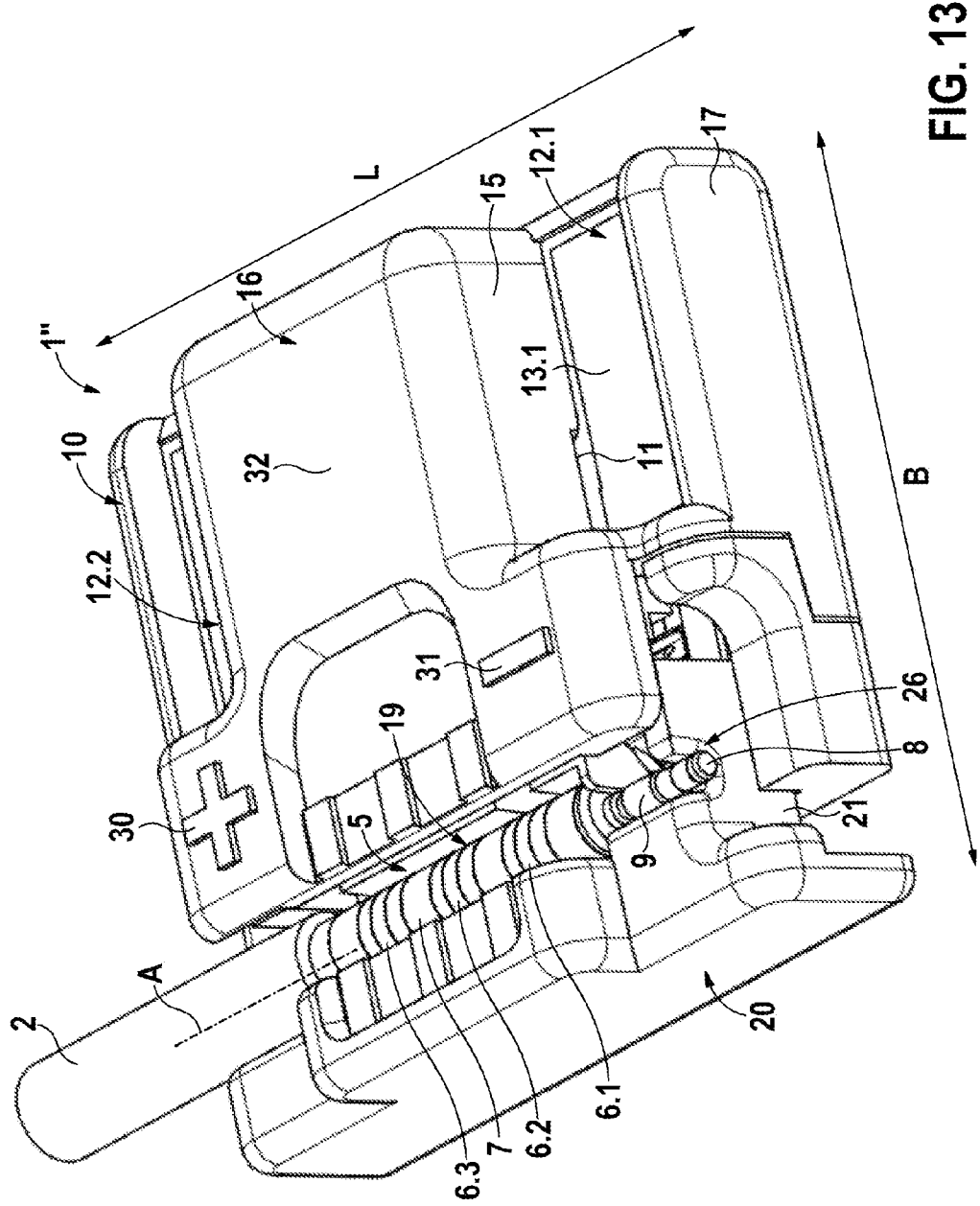
FIGS. 13-14 show perspective views, obliquely from above, of an adapter in a further embodiment, without the trigger button, comprising a connector in the open and contact positions of the adapter drawer.
Figure 14:
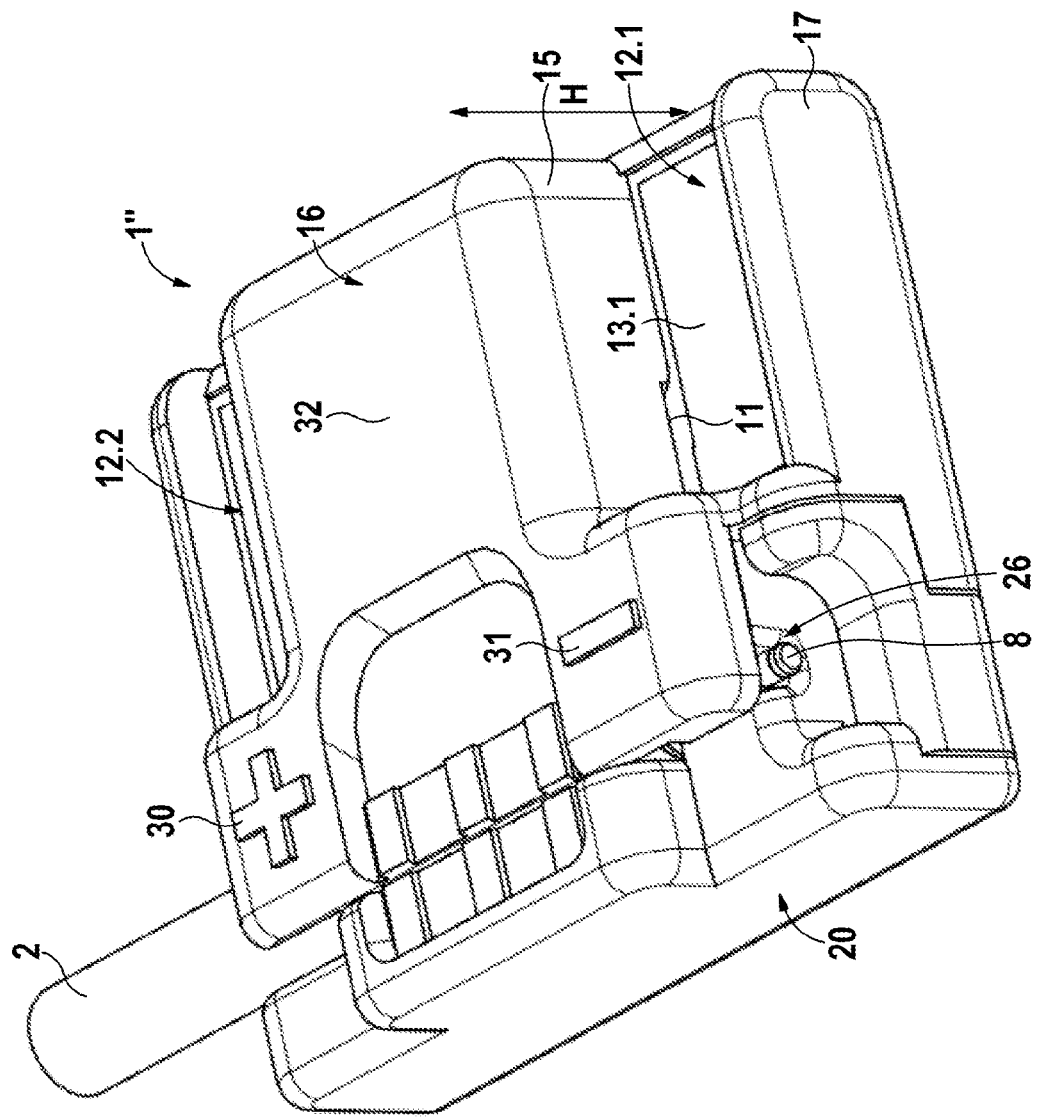

FIGS. 13-14 show a further embodiment of an adapter 1", which corresponds to the embodiment according to FIGS. 1-7. The only difference is that the trigger button 22 for removing the latching engagement of the drawer 20 in the open and contact positions has been omitted. Analogous to the exemplary embodiment according to FIGS. 8-12, these latching engagements can be overcome by simply pulling or pressing on the drawer 20.

Figure 15:
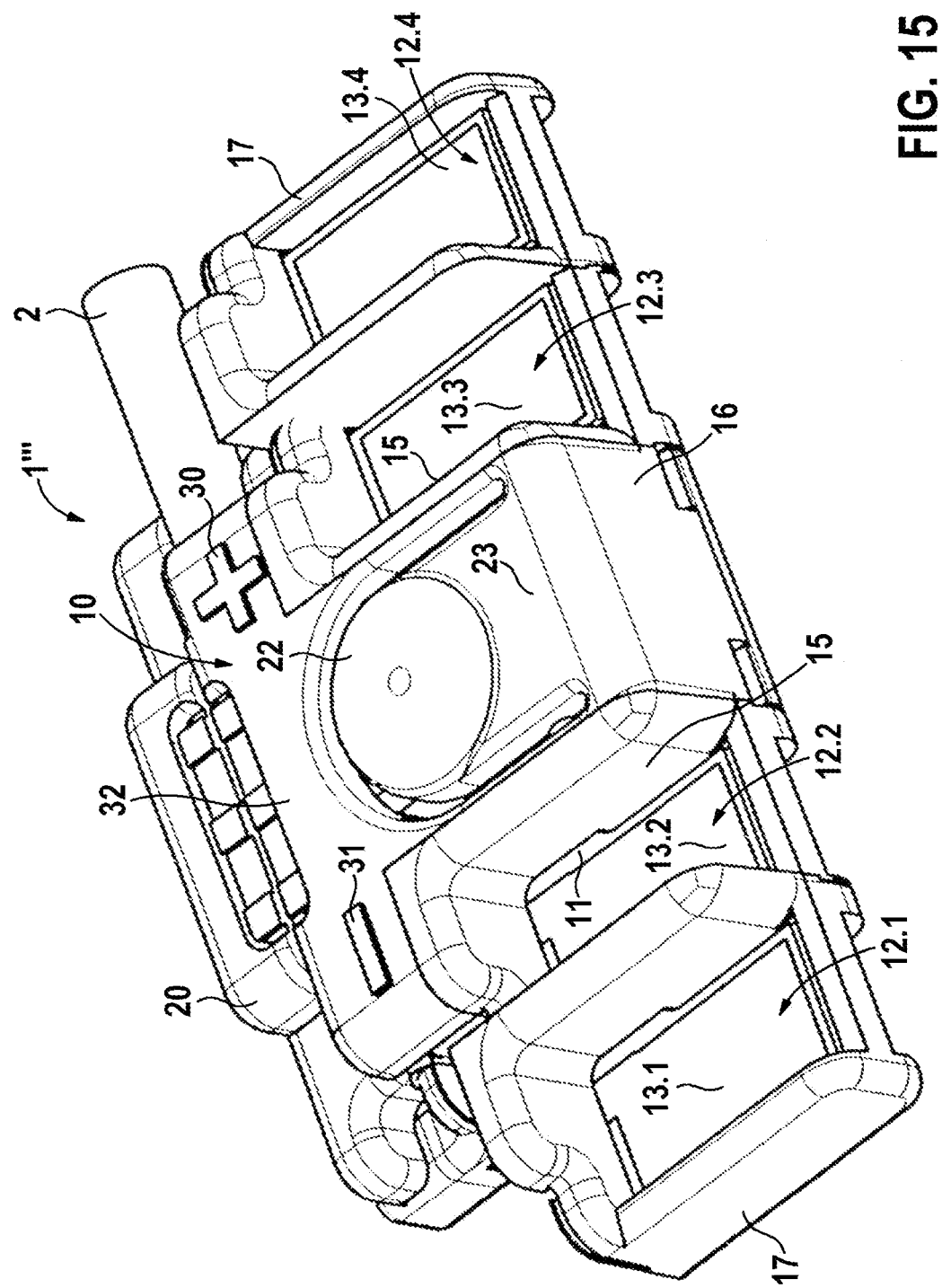
FIG. 15 is a perspective view of an adapter in a further embodiment, comprising four contact elements.

FIG. 15 finally shows an adapter 1''', which in the basic design corresponds to the adapter 1 according to FIGS. 1-7, however, it is designed to contact all four connecting contacts 6.1 to 6.4 of the connector 5. Components that correspond with those of the adapter 1 have been provided with identical reference numerals and do not require explanation again. In contrast to the aforementioned exemplary embodiment, the variant of the adapter 1' according to FIG. 15, however, shows four contact elements 12.1 to 12.4 on the circuit board 11, with correspondingly exposed contact surfaces 13.1 to 13.4, at which respective alligator clips can be placed. Analogous to FIG. 6, in the interior of the adapter housing 10, the contact elements 12.1 to 12.4 on the circuit board 11 are connected to spring contacts, which can be brought in electrical connection with the individual connecting contacts 6.1 to 6.4 in the closed position of the adapter 1' shown in FIG. 15.

Finally, all four exemplary embodiments of the adapter 1, 1', 1", 1' have in common that the adapter housing 10 is provided with polarity symbols 30 and 31 of "+" and "−", respectively, which are associated with the respective contact surfaces 13.1, 13.2. The polarity symbols 30, 31 are designed in a raised manner on the upper face 32 of the structure 16 of the adapter housing 10.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. An adapter for mechanically and electrically connecting an implantable electrode, by means of a proximal connector thereof comprising at least one connecting contact for an electrode surface of the electrode, to at least one test terminal contact, in the form of an alligator clip, of a measuring device, the adapter comprising:
    an adapter housing made of an electrically insulating material;
    a receiving element for the proximal connector which is adapted to a shape of the proximal connector;
    at least one contact element disposed in the adapter housing for establishing contact between the at least one connecting contact of the proximal connector and the at least one test terminal contact; and
    a receiving tray mounted on the adapter housing so as to be variable between an open position and a closed contact position and in which the receiving element for the proximal connector is disposed, wherein:
        in the open position, the proximal connector is insertable in the receiving element in a defined position and is removable therefrom; and
        by transferring the receiving tray into the contact position, the at least one connecting contact of the proximal connector enables contact with the contact element in the adapter housing in a defined manner,
    wherein the receiving tray is a drawer that is displaceable between the open position and the contact position on the adapter housing, and
    wherein the displacement direction of the drawer is transversely to a longitudinal direction of the proximal connector.

2. The adapter according to claim 1, wherein the receiving tray can be fixed in the open position and/or contact position relative to the adapter housing by a latching engagement.

3. The adapter according to claim 2, wherein the latching engagement can be detached by way of a trigger button.

4. The adapter according to claim 3, wherein the trigger button is coupled to the adapter housing via a spring tongue.

5. The adapter according to claim 2, wherein the latching engagement comprises a detent tongue and projection disposed on the receiving tray configured to engage a detent recess disposed on the adapter housing.

6. The adapter according to claim 1, wherein the at least one connecting contact of the proximal connector is completely covered toward the outside in the contact position of the receiving tray.

7. The adapter according to claim 1, wherein, in front of the proximal connector positioned in the receiving tray, the receiving tray and the adapter housing are provided at their end faces with an opening to provide unobstructed access to a central electrode lumen guided through the proximal connector, both in the open position and in the contact position.

8. The adapter according to claim 7, wherein the opening is configured to enable at least one of manipulation and replacement of a mandarin without a change in position of the adaptor and the proximal connector.

9. The adapter according to claim 1, wherein the at least one contact element in the adapter housing has an outwardly exposed contact surface for the at least one test terminal contact.

10. The adapter according to claim 1, wherein a guide for the at least one test terminal contact flanks a surface of the at least one test terminal contact.

11. The adapter according to claim 1, wherein, in an adapter for the proximal connector comprises connectors comprising a plurality of connecting contacts, the receiving tray and the adapter housing are designed for the electrical connection of two or four connecting contacts to two test terminal contacts, in each case via a contact element.

12. The adapter according to claim 11, wherein a polarity symbol is associated in each case with the contact elements.

13. The adapter according to claim 11, wherein a polarity symbol is associated in each case with exposed contact surfaces of the contact elements.

14. The adapter according to claim 1, wherein the adapter housing comprises more than four contact elements for connecting test terminal contacts.

15. The adapter according to claim 1, wherein the adapter housing comprises eight contact elements for connecting test terminal contacts.

16. The adapter according to claim 1, further comprising at least one circuit board disposed on the adapter housing, each individual circuit board having two metallic strip contact elements.

17. The adapter according to claim 1, further comprising at least one ridge-shaped configuration disposed on a face of the adapter housing, wherein the at least one ridge-shaped configuration is configured to prevent alligator clips that have been attached to the adapter from sliding off.

* * * * *